United States Patent [19]
Kohjiya et al.

[11] Patent Number: 5,837,157
[45] Date of Patent: Nov. 17, 1998

[54] POLYMER SOLID ELECTROLYTE

[75] Inventors: Shinzo Kohjiya; Yuko Ikeda, both of Kyoto; Katsuhito Miura, Sanda; Shigeru Shoji, Amagasaki; Yasuo Matoba, Nishinomiya; Masayoshi Watanabe, Yokohama; Takahiro Sakashita, Osaka, all of Japan

[73] Assignee: Daiso Co., Ltd., Osaka-Fu, Japan

[21] Appl. No.: 959,707

[22] Filed: Oct. 27, 1997

Related U.S. Application Data

[63] Continuation of Ser. No. 643,882, May 7, 1996, abandoned.

[30] Foreign Application Priority Data

| May 8, 1995 | [JP] | Japan | 7-109616 |
| Feb. 15, 1996 | [JP] | Japan | 8-027896 |
| Apr. 2, 1996 | [JP] | Japan | 8-079898 |

[51] Int. Cl.⁶ .................................................. H01M 6/18
[52] U.S. Cl. .................... 252/62.2; 429/190; 429/192; 361/525
[58] Field of Search .......................... 252/62.2; 429/190, 429/192; 361/525

[56] References Cited

U.S. PATENT DOCUMENTS

| 4,303,748 | 12/1981 | Armand et al. | 429/192 |
| 4,822,701 | 4/1989 | Ballard et al. | 429/192 |
| 5,162,174 | 11/1992 | Andrei et al. | 429/192 |
| 5,527,639 | 6/1996 | Noda et al. | 429/192 |

FOREIGN PATENT DOCUMENTS

| 1269702 | 5/1990 | Canada . |
| 0 174 894 | 3/1986 | European Pat. Off. . |
| 0 460 876 | 5/1991 | European Pat. Off. . |
| 0 585 072 | 3/1994 | European Pat. Off. . |
| 2693731 | 1/1994 | France . |
| 63-154736 | 6/1988 | Japan . |

OTHER PUBLICATIONS

Abstracts of Japan, vol. 012, No. 426, re JP 63–154736 dated 28 Jun. 1988.
"Ionic Conductivity inOrganic Solids Derived from Amorphous Macromolecules", D.G.H. Ballard, P.Cheshire, T.S. Mann and J.E. Przeworski, Macromolecules 1990, 23, pp. 1256–1264 (Month Unknown).
Patent Abstracts of Japan re Japanese Publication No. 04036347, published Feb. 1992 entitled "Ionically Conductive Polyelectrolyte".
Patent Abstracts of Japan re Japanese Publication No. 03200865, published Sep. 1991 entitled "Ionically Conductive Polyelectrolyte".
Patent Abstracts of Japan re Japanese Publication No. 04068064, published Mar. 1992 entitled "Polyelectrolyte Having Ionic Conductivity".
Patent Abstracts of Japan re Japanese Publication No. 03200864, published Sep. 1991 entitled "Ionically Conductive Polyelectrolyte",
Patent Abstracts of Japan re Japanese Publication No. 03200863, published Sep. 1991 entitled "Ionically Conductive Polyelectrolyte".
Patent Abstracts of Japan re Japanese Publication No. 03047833 published Feb. 1991 entitled "Ion–Conducting Polymeric Electrolyte".
Motogami, et al., "A New Polymer Electrolyte Based on Polyglycidylether", *Electrochimica Acta*, vol. 37, No. 9 (1992), pp. 1725–1727 (Month Unknown).
Kono, et al., "Synthesis of Polymer Electrolytes Based on Poly[2–(2–methoxyethoxy)ethyl glycidyl ether] and Their High Ionic Conductivity", *Polymers for Advanced Technologies*, vol. 4 (1993), pp. 85–91 (Month Unknown).

*Primary Examiner*—Alan Diamond
*Attorney, Agent, or Firm*—Merchant, Gould, Smith, Edell, Welter & Schmidt

[57] ABSTRACT

A polymer solid electrolyte which is superior to a conventional solid electrolyte in ion conductivity and also superior in processing characteristics, molding characteristics, mechanical strength and flexibility. The polymer solid electrolyte produced by formulating a soluble electrolyte salt compound to a polyether copolymer having an oligooxyethylene side chain and an electrolyte salt compound which is soluble in the polyether copolymer, the polyether polymer being a solid random copolymer having a main chain structure consisting of 5 to 30 molar % of a structural unit of the following formula (1) and 95 to 70 molar % of a structural unit of the following formula (2), and the polyether polymer having a polymerization degree n of an oxyethylene unit of the side chain part of the formula (1) of 1 to 12, a number-average molecular weight of 100,000 to 2,000,000, a glass transition point measured by a differential scanning calorimeter (DSC) of not more than −60° C. and a melting calorie of not more than 70 J/g.

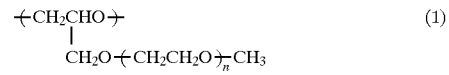

(1)

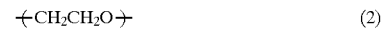

(2)

13 Claims, No Drawings

POLYMER SOLID ELECTROLYTE

This is a Continuation of application Ser. No. 08/643,882, filed 7 May 1996 now abandoned.

FIELD OF THE INVENTION

The present invention relates to a polymer solid electrolyte. More particularly, it relates to a polymer solid electrolyte which is suitable as a material for electrochemical device such as battery, capacitor, sensor, etc.

BACKGROUND OF THE INVENTION

Heretofore, an electrolyte constituting an electrochemical device such as battery, capacitor, sensor, etc. has been used in the form of a solution or paste in view of an ion conductivity. However, a device is likely to be damaged due to leakage of liquid and a separator to be impregnated with an electrolyte solution is required and, therefore, problems such as limitation of ultra-miniaturization and thin volume is pointed out. To the contrary, a solid electrolyte such as inorganic crystalline substance, inorganic glass, organic polymer substance, etc. is suggested. The organic polymer substance is normally superior in processing characteristics and molding characteristics and the resulting solid electrolyte has a flexibility and bending processing characteristics. Therefore, design freedom of the device for which the solid electrolyte is applied becomes large and the development thereof is expected. However, the solid electrolyte is inferior to other materials in ion conductivity at present.

For example, a trial of formulating a specific alkaline metal salt into a mixture of an epichlorohydrin rubber and a low-molecular weight polyethylene glycol derivative and applying the resultant to a polymer solid electrolyte is suggested in Japanese Laid-Open Patent Publication No. 2-235957 by the present applicant, but a conductivity value which is sufficient for practical use has not been obtained yet.

The polymer solid electrolyte obtained by crosslinking a polymer compound having an average-molecular weight of 1,000 to 20,000 described in Japanese Laid-Open Patent Publication Nos. 3-47833 and 4-68064 shows a comparatively good ion conductivity within a practical temperature, but an improved ion conductivity is further requested.

The polyether copolymer having an oligooxyethylene side chain described in Japanese Laid-Open Patent Publication Nos. 63-154736 and 63-241026 of the present applicant and European Patent Publication No. 434011 of the present applicant suggests the application for the polymer solid electrolyte or destaticizing material for plastic, but it is not described and suggested that those having a specific side chain length and a specific copolymer composition have specifically excellent properties as an ion conductive solid electrolyte.

The present inventors have found that, by formulating a soluble electrolyte salt compound into a polyether copolymer having a specific composition ratio wherein oligoethylene glycol glycidyl ether is used in combination with ethylene oxide as the copolymerization component, a solid electrolyte having an extremely increased ion conductivity as compared with those using the other epoxide (e.g. propylene oxide, epichlorohydrin, etc.) in combination can be obtained.

OBJECTS OF THE INVENTION

One object of the present invention is to provide a polymer solid electrolyte which is superior to a conventional solid electrolyte in ion conductivity and also superior in processing characteristics, molding characteristics, mechanical strength and flexibility.

Another object of the present invention provides a battery using the polymer solid electrolyte.

These objects as well as other objects and advantages of the present invention will become apparent to those skilled in the art from the following description.

SUMMARY OF THE INVENTION

The present invention provides a polymer solid electrolyte comprising a polyether copolymer having an oligooxyethylene side chain and an electrolyte salt compound which is soluble in the polyether copolymer, the polyether polymer being a solid random copolymer having a main chain structure consisting of 5 to 30 molar % of a structural unit of the following formula (1) and 95 to 70 molar % of a structural unit of the following formula (2), and the polyether polymer having a polymerization degree n of an oxyethylene unit of the side chain part of the formula (1) of 1 to 12, a number-average molecular weight of 100,000 to 2,000,000, a glass transition point measured by a differential scanning calorimeter (DSC) of not more than −60° C. and a heat of fusion of not more than 70 J/g.

The present invention also provide a battery using the polymer solid electrolyte.

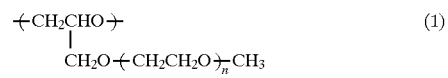  (1)

  (2)

DETAILED DESCRIPTION OF THE INVENTION

The process for producing the polyether copolymer having an oligooxyethylene side chain (hereinafter referred to as a polyether copolymer) used in the present invention is described in the above-described Japanese Laid-Open Patent Publication No. 63-154736. That is, it is obtained by reacting the respective monomers corresponding to the above formulas (1) and (2) with stirring at a reaction temperature of 10° to 80° C. in the presence or absence of a solvent, using a catalyst comprising mainly organic aluminum, a catalyst comprising mainly organic zinc, an organic tin-phosphate condensate catalyst, etc. as a catalyst for ring opening polymerization.

As the polyether copolymer used in the present invention, those whose molar ratio of the structural units (1) and (2) is respectively 5 to 30 molar % (preferably from 10 to 30 molar %) and 95 to 70 molar % (preferably from 90 to 70 molar %) are suitable. When the molar ratio of the structural unit (2) exceeds 95 molar %, an increase in glass transition point and crystallization of the structural unit of the formula (2) arise. Therefore, it becomes impossible to maintain the glass transition temperature at not more than −60° C. and the fusion heat not more than 70 J/g. As a result, the ion conductivity of the solid electrolyte is drastically lowered. It is normally known that the ion conductivity is improved by lowering crystallizability of ethylene oxide. It has been found that the effect of improving the ion conductivity is markedly large in case of the polyether copolymer of the present invention. On the other hand, when the molar ratio of the structural unit of the formula (2) is less than 70 molar %, a softening temperature of the copolymer is decreased and it becomes difficult to obtain a solid electrolyte at room temperature (e.g. 20° C., etc.). The above glass transition temperature and fusion heat are measured by a differential scanning calorimeter (DSC). In the present invention, those having the glass transition point of not more than −60° C. (preferably not more than −65° C.) and melting calorie of not more than 70 J/g (preferably not more than 50 J/g) are suitable for use. The ion conductivity is lowered by those whose glass transition point and melting calorie exceed the above value.

In the present invention, the polymerization degree n of the oxyethylene unit of the side chain part of the formula (1) of the polyether copolymer is preferably from 1 to 12, more preferably 2 or 3. When it exceeds 12, the ion conductivity of the resulting solid electrolyte is lowered, and it is not preferred. The number-average molecular weight of the polyether copolymer is from 100,000 to 2,000,000, preferably 200,000 to 1,500,000, so as to obtain satisfactory processing characteristics, molding characteristics, mechanical strength and flexibility. When the number-average molecular weight is smaller than 100,000, the resulting electrolyte becomes liquid and, therefore, leakage of liquid arises, and it is not preferred. On the other hand, when it exceeds 2,000,000, a problem arises in processing characteristics and molding characteristics.

The electrolyte salt compound used in the present invention may be any one which is soluble in the polyether copolymer in the present invention, and the following compound is preferably used.

That is, it is a compound comprising 1) a cation selected from metal cation, ammonium ion, amidinium ion and guanidium ion and 2) an anion selected from chloride ion, bromide ion, iodide ion, perchloric ion, thiocyanic ion, tetrafluoroboric ion, nitric ion, $AsF_6^-$, $PF_6^-$, stearylsulfonic ion, octylsulfonic ion, dodecylbenzenesulfonic ion, naphthalenesulfonic ion, dodecylnaphthalenesulfonic ion, 7,7,8,8-tetracyano-p-quinodimethane ion, $R_1SO_3^-$, $(R_1SO_2)(R_2SO_2)N^-$, $(R_1SO_2)(R_2SO_2)(R_3SO_2)C^-$ and $(R_1SO_2)(R_2SO_2)YC^-$, wherein each of $R_1$, $R_2$, $R_3$ and $Y$ is an electron attracting group. Preferably, $R_1$, $R_2$ and $R_3$ independently indicate a perfluoroalkyl or perfluoroaryl group having 1 to 6 carbon atoms, and $Y$ is a nitro group, a nitroso group, a carbonyl group, a carboxyl group, a cyano group or a trialkylammonium group. $R_1$, $R_2$ and $R_3$ may be the same or different.

As the metal cation, a cation of a transition metal can be used. Preferably, a cation of a metal selected from Mn, Fe, Co, Ni, Cu, Zn and Ag. Even when using a cation of a metal selected from Li, Na, K, Rb, Cs, Mg, Ca and Ba, preferred results can be obtained. It is possible to use two or more sorts of the above compounds in combination as the electrolyte salt compound. Among them, $LiPF_6$, $LiClO_4$ and lithium bistrifluoromethanesulfonylimide (hereinafter referred to as LiTFSI) are preferred in the case of a secondary lithium battery because no substantial glass transition point increase is seen with addition of such electrolytes.

In the present invention, the amount of the soluble electrolyte salt compound used for the total number of ethylene oxide unit in the main chain and side chain of the polyether copolymer, i.e. a ratio of the number of moles of the electrolyte salt compound to the total number of moles of ethylene oxide is within the range from 0.0001 to 5, preferably from 0.001 to 0.5. When this value exceeds 5, the processing characteristics, molding characteristics as well as mechanical strength and flexibility of the resulting solid electrolyte are lowered, and the ion conductivity is also lowered.

The process for producing the polymer solid electrolyte of the present invention is not specifically limited, but the polymer solid electrolyte is produced by mechanically mixing the respective components, or dissolving them in a solvent and removing the solvent. As means for mechanically mixing, there can be optionally used various kneaders, open rolls, extruders, etc. When it is produced by using the solvent, various polar solvents such as tetrahydrofuran, acetone, acetonitrile, dimethylformamide, dimethyl sulfoxide, dioxane, methyl ethyl ketone, methyl isobutyl ketone, etc. are used alone or in combination thereof. The concentration of the solution is not specifically limited, but is preferably from 1 to 50% by weight. If necessary, the solid electrolyte may also be crosslinked. Examples of the crosslinking agent in case of crosslinking the copolymer include tolylene-2,4-diisocyanate, tolylene-2,6-diisocyanate, 4-4-diphenylmethane diisocyanate, hexamethylene diisocyanate, etc.

When using the polymer solid electrolyte of the present invention, there can be easily obtained a solid electrolyte in the shape of a large-surface area thin film, which has a flexibility as a merit of the polymer. For example, it is possible to produce a battery using the polymer electrolyte of the present invention. In this case, examples of the positive electrode material include lithium-manganese complex oxide, lithium cobaltate, vanadium pentoxide, polyacene, polypyrene, polyaniline, polyphenylene, polyphenylene sulfide, polyphenylene oxide, polypyrrole, polyfuran, polyazulene, etc. Examples of the negative electrode material include interlaminar compound wherein lithium is occluded between layers of graphite or carbon, lithium metal, lithium-lead alloy, etc. One embodiment of the battery is shown in Example 8. It can also be used as a permeable membrane of an ion electrode of a cation such as alkaline metal ion, Cu ion, Ca ion, Mg ion etc. by making of its high electric conductivity.

The polymer solid electrolyte of the present invention is superior in processing characteristics, molding characteristics, mechanical strength and flexibility, and the ion conductivity is remarkably improved. Accordingly, it is expected to be applied for solid battery, large-capacity condenser and display device (e.g. electronic equipment such as electrochromic display, etc.).

The following Examples and Comparative Examples further illustrate the present invention in detail but are not to be construed to limit the scope thereof.

EXAMPLES 1 TO 4 AND COMPARATIVE EXAMPLES 1 TO 5

A polyether copolymer of Table 1 (1 g) (polyethylene oxide in case of Comparative Example 3) was dissolved in tetrahydrofuran (20 ml), and then the resulting solution was mixed with a tetrahydrofuran solution of lithium perchloride so that a ratio of the number of moles of a soluble electrolyte salt compound to the number of moles of an ethylene oxide becomes 0.005. This mixed solution was casted on a mold made of polytetrafluoroethylene, followed by sufficient drying to obtain a film.

The results of Examples and Comparative Examples are shown in Table 1. In Table 1, the glass transition temperature and the fusion heat were measured respectively in a nitrogen atmosphere under the condition of a temperature within the range of −100° to 80° C. and a heating rate of 10° C./minute, using a differential scanning calorimeter DSC8230B (manufactured by Rigaku Denki Co., Ltd.). The conductivity a was measured by using platinum as an electrode under the condition of a voltage of 0.5 V and a frequency within the range of 5 Hz to 1 MHz (A.C. method) according to a complex impedance calculation method.

EXAMPLE 5

A polyether copolymer (1 g) comprising 5 molar % of the structural unit of the formula (1) and 95 molar % of the structural unit of the formula (2) was dissolved in acetonitrile (20 ml), and then the resulting solution was mixed with an acetonitrile solution of LiTFSI so that a ratio of the number of moles of LiTFSI to the number of an ethylene oxide unit becomes 0.005. This mixed solution was cast on a mold made of polytetrafluoroethylene, followed by sufficient drying to obtain a film. According to the same manner as that described in Examples 1 to 4, characteristics of the film were measured. The conductivity of the solid electrolyte at 30° C. was $4.0 \times 10^{-4}$ S/cm.

It is apparent from a comparison with the Comparative Examples that the electrolyte of the present invention has an excellent conductivity.

EXAMPLE 6

A polyether copolymer (1 g) comprising 12 molar % of the structural unit of the formula (1) and 88 molar % of the structural unit of the formula (2) was dissolved in acetonitrile (20 ml), and then the resulting solution was mixed with an acetonitrile solution of LiTFSI so that a ratio of the number of moles of LiTFSI to the number of an ethylene oxide unit becomes 0.003. This mixed solution was cast on a mold made of polytetrafluoroethylene, followed by sufficient drying to obtain a film. According to the same manner as that described in Examples 1 to 4, characteristics of the film were measured.

EXAMPLE 7

A film was obtained by a same method as the above Example 6 except that a ratio of the number of moles of LiTFSI to the number of an ethylene oxide unit was 0.05. According to the same manner as that described in Examples 1 to 4, characteristics of the film were measured.

EXAMPLE 8

A secondary battery was produced by using the polymer solid electrolyte obtained in Example 3 as the electrolyte, a lithium metal foil as the negative electrode and lithium cobaltate ($LiCoO_2$) as the positive electrode. The size of the polymer solid electrolyte is 10 mm×10 mm×1 mm. The size of the lithium foil is 10 mm×10 mm×0.1 mm. Lithium cobaltate was prepared by mixing a predetermined amount of lithium carbonate and cobalt carbonate powder and calcining the mixture at 900° C. for 5 hours. The resulting lithium cobaltate was pulverized and a proper amount of acetylene black is added thereto for improving the conductivity and then subjected to press molding under a pressure of 300 Kgw/cm$^2$ to form a positive electrode for battery of 10 mm×10 mm×2 mm.

The polymer solid electrolyte obtained in Example 3 was interposed between the lithium metal foil and lithium cobaltate plate and charging/discharging characteristics of the battery was examined while applying a pressure of 10 Kgw/cm$^2$ so that the interface of them is closely adhered. The discharging current at the initial terminal voltage of 3.2 V was 0.4 mA/cm$^2$ and charging could be conducted at 0.3 mA/cm$^2$. In this Example, an extremely thin battery can be produced and, therefore, the resulting battery is lightweight and has a large capacity.

TABLE 1

| | Example No. | | | | | | |
|---|---|---|---|---|---|---|---|
| | 1 | 2 | 3 | 4 | 5 | 6 | 7 |
| Composition (molar %) of copolymer | | | | | | | |
| Ethylene oxide | 79 | 90 | 95 | 93 | 95 | 88 | 88 |
| Propylene oxide | | | | | | | |
| Epichlorohydrin | | | | | | | |
| Structural unit of the formula (1) | 21 | 10 | 5 | 7 | 5 | 12 | 12 |
| Polymerization degree of ethylene oxide of the side chain part (n) | 2 | 2 | 2 | 8.5 | 2 | 3 | 3 |
| Number-average molecular weight of copolymer | 250,000 | 300,000 | 1,100,000 | 200,000 | 1,100,000 | 700,000 | 700,000 |
| Glass transition temperature (°C.) | −69 | −67 | −61 | −67 | −61 | −68 | −68 |
| Melting calorie (J/g) | 17 | 48 | 67 | 58 | 67 | 44 | 44 |
| Conductivity of solid electrolyte film σ (S/cm) 30° C. | $9.2 \times 10^{-4}$ | $8.9 \times 10^{-4}$ | $1.1 \times 10^{-4}$ | $6.3 \times 10^{-4}$ | $4.0 \times 10^{-4}$ | $7.8 \times 10^{-4}$ | $2.1 \times 10^{-3}$ |

| | Comparative Example No | | | | |
|---|---|---|---|---|---|
| | 1 | 2 | 3 | 4 | 5 |
| Composition (molar %) of copolymer | | | | | |
| Ethylene oxide | 93 | 58 | 100 | | |
| Propylene oxide | | | | 89 | |
| Epichlorohydrin | | | | | 82 |
| Structural unit of the formula (1) | 7 | 42 | | 11 | 18 |
| Polymerization degree of ethylene oxide of the side chain part (n) | 20 | 2 | | 2 | 2 |
| Number-average molecular weight of copolymer | 250,000 | 200,000 | 200,000 | 250,000 | 250,000 |
| Glass transition temperature (°C.) | −63 | −70 | −59 | −66 | −31 |
| Melting calorie (J/g) | 82 | 3 | 164 | 0 | 0 |
| Conductivity of solid electrolyte film σ (S/cm) 30° C. | $9.2 \times 10^{-5}$ | Pasty | $1.4 \times 10^{-6}$ | $2.2 \times 10^{-8}$ | $1.8 \times 10^{-9}$ |

What is claimed is:

1. A polymer solid electrolyte, comprising a polyether copolymer having an oligooxyethylene side chain and an electrolyte salt compound soluble therein, wherein said polyether copolymer is a solid random copolymer having a main chain structure consisting of 5 to 30 molar % of a structural unit of the following formula (1) and 95 to 70 molar % of a structural unit of the following formula (2),

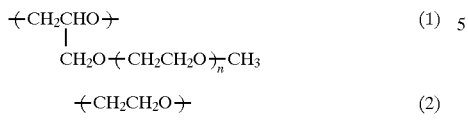  (1)

$\text{-(CH}_2\text{CH}_2\text{O)-}$  (2)

wherein n is 1 to 12, and the polyether copolymer has a number-average molecular weight of 100,000 to 2,000,000, a glass transition temperature measured by a differential scanning calorimeter (DSC) of not more than $-60°$ C. and a heat of fusion of not more than 70 J/g.

2. The polymer solid electrolyte according to claim 1, wherein the polyether copolymer has a main chain structure consisting of 10 to 30 molar % of the structural unit of the formula (1) and 90 to 70 molar % of the structural unit of the formula (2).

3. The polymer solid electrolyte according to claim 1, wherein the polyether copolymer has a glass transition temperature of not more than $-65°$ C. and a heat of fusion of not more than 50 J/g.

4. The polymer solid electrolyte according to claim 1, wherein the electrolyte salt compound is a compound comprising a cation selected from metal cation, ammonium ion, amidinium ion and guanidium ions and an anion selected from chloride ion, bromide ion, iodide ion, perchloric ion, thiocyanic ion, tetrafluoroboric ion, nitric ion, $AsF_6^-$, $PF_6^-$, stearylsulfonic ion, octylsulfonic ion, dodecylbenzenesulfonic ion, naphthalenesulfonic ion, dodecylnaphthalenesulfonic ion, 7,7,8,8-tetracyano-p-quinodimethane ion, $R_1SO_3^-$, $((R_1SO_2)(R_2SO_2)N)^-$, $((R_1SO_2)(R_2SO_2)(R_3SO_2)C)^-$ and $((R_1SO_2)(R_2SO_2) Y C)^-$, wherein each of $R_1$, $R_2$, $R_3$ and Y is an electron attracting group.

5. The polymer solid electrolyte according to claim 4, wherein $R_1$, $R_2$ and $R_3$ independently indicate a perfluoroalkyl or perfluoroaryl group having 1 to 6 carbon atoms, and Y is a nitro group, a nitroso group, a carbonyl group, a carboxyl group, or a cyano group.

6. The polymer solid electrolyte according to claim 4, wherein the metal cation is a cation of a metal selected from the group consisting of Li, Na, K, Rb, Cs, Mg, Ca and Ba.

7. The polymer solid electrolyte according to claim 4, wherein the metal cation is a cation of a transition metal.

8. The polymer solid electrolyte according to claim 4, wherein the metal cation is a cation of a metal selected from the group consisting of Mn, Fe, Co, Ni, Cu, Zn and Ag.

9. The polymer solid electrolyte according to claim 1, wherein the polyether copolymer has a number-average molecular weight of 200,000 to 1,500,000.

10. The polymer solid electrolyte according to claim 1, wherein the polymer solid electrolyte has a formulation ratio defined as the number of moles of the electrolyte salt compound to the total number of moles of ethylene oxide units in said polyether copolymer, and said formulation ratio ranges from 0.0001 to 5.

11. A battery comprising a polymer solid electrolyte, said polymer solid electrolyte comprising a polyether copolymer having an oligooxyethylene side chain and an electrolyte salt compound soluble therein, wherein said polyether copolymer is a solid random copolymer having a main chain structure consisting of 5 to 30 molar % of a structural unit of the following formula (1) and 95 to 70 molar % of a structural unit of the following formula (2),

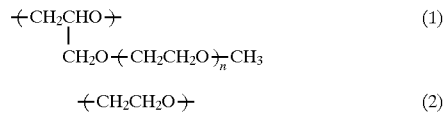  (1)

$\text{-(CH}_2\text{CH}_2\text{O)-}$  (2)

wherein n is 1 to 12, and the polyether copolymer has a number-average molecular weight of 100,000 to 2,000,000, a glass transition temperature measured by a differential scanning calorimeter (DSC) of not more than $-60°$ C and a heat of fusion of not more than 70 J/g.

12. The battery according to claim 11, wherein the electrolyte salt compound is selected from the group consisting of $LiPF_6$, $LiClO_4$ and lithium bistrifluoromethanesulfonylimide.

13. The battery according to claim 11, wherein n is 2 or 3.

* * * * *